United States Patent [19]

Frengen

[11] Patent Number: 5,739,042

[45] Date of Patent: Apr. 14, 1998

[54] METHOD OF ASSAY

[75] Inventor: Jomar Frengen, Trondheim, Norway

[73] Assignee: Sinvent AS, Trondheim, Norway

[21] Appl. No.: 663,121

[22] PCT Filed: Dec. 23, 1994

[86] PCT No.: PCT/GB94/02817

§ 371 Date: Sep. 6, 1996

§ 102(e) Date: Sep. 6, 1996

[87] PCT Pub. No.: WO95/17675

PCT Pub. Date: Jun. 29, 1995

[30] Foreign Application Priority Data

Dec. 23, 1993 [GB] United Kingdom ............... 9326238

[51] Int. Cl.$^6$ ................ G01N 33/543; G01N 33/537
[52] U.S. Cl. ............ 436/523; 422/61; 422/82.08; 435/7.1; 435/7.93; 435/7.94; 435/7.95; 435/962; 436/518; 436/523; 436/538; 436/824
[58] Field of Search ................ 422/61, 82.08; 435/7.1, 7.93, 7.94, 7.95, 287.1, 287.2, 287.9, 962; 436/518, 523, 538, 824

[56] References Cited

U.S. PATENT DOCUMENTS

| | | | |
|---|---|---|---|
| 4,244,940 | 1/1981 | Jeong et al. | 424/1 |
| 4,556,642 | 12/1985 | Collet-Cassart et al. | 436/500 |
| 4,590,169 | 5/1986 | Cragle et al. | 436/523 |
| 4,595,661 | 6/1986 | Cragle et al. | 436/534 |
| 4,665,020 | 5/1987 | Saunders | 435/7 |
| 4,680,274 | 7/1987 | Sakai et al. | 436/512 |
| 4,743,542 | 5/1988 | Graham et al. | |
| 5,047,321 | 9/1991 | Loken et al. | 435/6 |
| 5,064,770 | 11/1991 | DeLuca et al. | 436/542 |
| 5,206,177 | 4/1993 | DeLaCroix et al. | 436/518 |
| 5,451,508 | 9/1995 | Hoyle et al. | 435/7.93 |
| 5,561,070 | 10/1996 | Stewart et al. | 436/526 |
| 5,567,627 | 10/1996 | Lehnen | 436/518 |
| 5,585,241 | 12/1996 | Lindmo | 435/6 |

FOREIGN PATENT DOCUMENTS

| | | |
|---|---|---|
| 0 162 914 | 5/1989 | European Pat. Off. |
| 2 652 900 | 4/1991 | France . |
| 89/11101 | 11/1989 | WIPO . |

OTHER PUBLICATIONS

Frengen et al., Clinical Chemistry, vol. 39/10, 2174–2181, 1993.

Lindmo et al., Journal of Immunological Methods, vol. 126, 183–189, 1990.

*Primary Examiner*—Christopher L. Chin
*Assistant Examiner*—Bao-Thuy L. Nguyen
*Attorney, Agent, or Firm*—Bacon & Thomas

[57] ABSTRACT

The present invention relates to a binary assay method capable of providing wide dynamic range, a high degree of precision and rapid processing times in which analyte is reacted successively with two independently determinable forms of solid-supported binding partner and also with a labelled ligand having affinity for the analyte or binding partner. The analyte concentration is determined from signals deriving from the resulting two forms of analyte-binding partner-labelled ligand systems by reference to a double standard calibration curve. A kit for use in the method is also disclosed.

12 Claims, 2 Drawing Sheets

METHOD OF ASSAY

This invention relates to a method of assaying an analyte and to kits useful in such a method.

Assay techniques for determining the presence and desirably also the concentration of an analyte using a binding partner having specificity for that analyte are frequently encountered, e.g. in the fields of biochemistry and clinical chemistry. Thus, for example, a wide range of immunological and related techniques has been proposed for determining materials such as antigens in serum, using an appropriate binding partner for the analyte, such as a specific antibody (e.g. a monoclonal antibody) for a particular antigen.

One such technique comprises competitive binding assays, in which a known amount of a labelled version of an analyte to be determined (e.g. carrying a radioactive label) and a relatively small known amount of a binding partner therefor are incubated with the analyte to be determined, whereby the labelled and the naturally-occurring analyte compete for the binding partner. The amount of labelled analyte bound to the binding partner is thereafter determined and the concentration of the naturally-occurring analyte, which will bear an inverse relationship to this amount, is assessed from a previously established standard curve.

Another useful technique comprises sandwich assays. These employ an excess of binding partner, the analyte which binds thereto being labelled by treatment with a labelled ligand also having affinity for the analyte. The amount of bound and labelled analyte is then determined and permits the analyte concentration to be assessed by reference to a standard calibration curve.

The binding partner and the labelled ligand in such sandwich assays preferably have affinities for different binding sites (e.g. epitopes) on the analyte. The ligand may, for example, be labelled for reading on the basis of radioactivity, light absorption or fluorescence.

Sandwich assays tend to exhibit greater sensitivity than competitive binding assays and are therefore usually preferred. It will be appreciated that high sensitivity is essential in, for example, immunoassays in clinical laboratories, where it may be required to quantify e.g. antigens present in serum at concentrations in the nmol/l to pmol/l range or even lower.

The binding partner in both the above-described types of assay is commonly coupled to a solid support in order to facilitate isolation of the bound analyte and competing or analyte-bound label. Thus, for example, the binding partner may be coupled to the surface of a reaction vessel, e.g. to the surfaces of the wells of a microtitre plate made from a suitable plastics material, so as to facilitate washing to remove unbound excess labelled ligand.

Alternatively the binding partner may be coupled to the surfaces of an array of particles, for example made of a suitable plastics material such as polystyrene or polyacrylate. Separation of the bound analyte/label from free label may then be effected by, for example, filtration or, in the event that superparamagnetic particles are employed, by application of a magnetic field. The particles are advantageously of microscopic size in order to present a large total surface area coated with the binding partner. The use of monosized microparticles is preferred since it ensures that the particles exhibit standard binding properties.

A disadvantage of the above-described basic assay techniques is that separation of the bound analyte and label and associated washing steps to remove unbound label are inherently time-consuming and labour-intensive. It is known, however, that this problem may in principle be avoided in the case of particle-based assays if the particles are analysed by means of flow cytometry. This typically involves passage of a suspension of particles through the measurement region of a photometer in such a way that successive individual particles are irradiated with excitation light, causing emission of a pulse of scattered light related to the size of the particle and a further signal, e.g. a pulse of fluorescent light, related to the amount and nature of the label bound to the particle. Suitable electronic detectors and microprocessors classify and store the results, whereby measurements in respect of $10^4$–$10^5$ individual particles may readily be obtained in e.g. one minute of data acquisition time. Hydrodynamic focusing of the sample stream in a flow cytometer results in the measurement region (i.e. the volume of sample stream within the excitation/detection region) being very small, typically of the order of $(10 \ \mu m)^3$, so that the amount of unbound label present in the liquid surrounding an individual particle being measured will be insignificant. Accordingly there is no need to separate unbound label prior to the flow cytometric particle analysis, which is therefore said to be a homogeneous, i.e. separation free, assay.

A general problem associated with sandwich assays in particular, including those performed using flow cytometric techniques, is that their dynamic range is limited by a phenomenon known as the hook effect, which occurs at high analyte concentrations. Thus the binding partner is normally used in a fixed amount, the theoretical maximum detectable analyte concentration thus being determined by the total available binding capacity of the binding partner for the analyte. Since, however, the labelled ligand is also normally used in a fixed amount, the amount of label available per bound analyte molecule will effectively decrease when the analyte concentration exceeds this theoretical maximum, as a result of increasing binding of the label to excess unbound analyte remaining in solution. In other words, the unbound excess analyte competes with the bound analyte for the label and thereby reduces the amount of label immobilised on the bound analyte. This will lead to a decrease in the observed level of bound analyte/label as the analyte concentration increases above the level at which the binding partner becomes saturated. Accordingly, calibration curves of signal intensity in respect of bound label against analyte concentration rise to a maximum and then fall off as the analyte concentration increases further, with the result that signal intensities cannot unambiguously be ascribed to a single concentration value unless additional steps, e.g. involving dilution of the sample and further assaying, are carried out.

Whilst the onset of the hook effect can in principle be delayed by increasing the amount of binding partner used this will inevitably lead to reduced sensitivity at low analyte concentrations, since measurement techniques such as flow cytometry require a certain minimum level of bound analyte/label per particle to give accurately detectable results.

U.S. Pat. No. 4,595,661 suggests that the hook effect in an immunoassay may be reduced by using an additional antibody, which may optionally be labelled and/or bound to a solid carrier, and which has a lower affinity for the target antigen than the primary binding partner antibody and labelled ligand. Although this low affinity antibody may delay onset of the hook effect by binding with the analyte at high analyte concentrations, its presence will again reduce the sensitivity of the assay at low analyte concentrations as a result of increased background interference, non-specific binding etc.

A similar approach is described in U.S. Pat. No. 4,743,542, where the principle is again to add unlabelled antibody in competition with the labelled ligand in an immunoassay. By acting as an additional reagent for the antigen, this unlabelled antibody raises the antigen concentration at which saturation of the primary binding partner antibody occurs, and so postpones onset of the hook effect. The overall effect is to give a calibration curve covering a wider range of antigen concentrations but having a reduced slope, with the consequent disadvantage of a larger uncertainty in any determined antigen concentration.

WO-A-8911101 describes a more sophisticated assay technique which utilises high and low affinity binding partners respectively coated onto different types of monodisperse particles which are distinguishable by flow cytometry. Predetermined amounts of this binary particle mixture and of labelled ligand are incubated with the analyte, and the resulting two types of labelled ligand-carrying particles are thereafter independently but simultaneously detected by means of a flow cytometer, the analyte concentration being determined from the thus-obtained two measurement values by reference to a double standard calibration curve.

This dual affinity assay technique may be applied both to competitive binding assays, in which case the labelled ligand should have affinity for the binding partner, typically being a labelled version of the analyte, and to sandwich assays, in which case the labelled ligand should have affinity for the analyte. It is possible simultaneously to assay a plurality of analytes using a plurality of binary particle mixtures such that all the particle types are separately distinguishable by the flow cytometer.

The use of a double standard calibration curve enhances the precision of the assay and enables immediate detection of anomalous or incorrect results, since the two measurement values for a sample must fit as a pair to the double curve. Because the two types of particles are separately determined sensitivity at low concentrations, which is principally a function of the high affinity binding partner, is not compromised by the presence of the low affinity binding partner, which in turn permits high precision measurements at high analyte concentration and enhances the dynamic range of the assay by forestalling the hook effect. This may be contrasted with the immunoassay described in U.S. Pat. No. 4,595,661 which, when a labelled additional antibody is used, measures only the sum of the contributions from the two binding reactions, leading to reduced sensitivity at low antigen concentrations.

The present invention is based on the surprising finding that a wide dynamic working range coupled with a high degree of precision and rapid processing time may be achieved with a variety of binary assay systems, i.e. systems in which two independently determinable forms of binding partner are used and the analyte concentration is obtained from readings derived from these two forms by means of a double standard curve, if the two forms of binding partner are reacted successively rather than simultaneously with the analyte and labelled ligand.

Thus according to one aspect of the present invention there is provided a method for assaying an analyte in a sample comprising reacting the sample with two independently determinable forms of solid-supported binding partner having affinity for the analyte and with a labelled ligand having affinity for the analyte or the binding partner, said two independently determinable forms of solid-supported binding partner being such that signals in respect of the resulting two forms of labelled ligand-carrying solid-supported binding partner may be independently determined whereby the analyte concentration may be obtained by reference to a double standard calibration curve, characterised in that the sample is reacted with the first form of solid-supported binding partner and after an appropriate interval with the second form of solid-supported binding partner.

A number of different assay systems and detection techniques may be used in the method of the invention. Thus, for example, the two forms of solid-supported binding partner may comprise binding partner-coated monodisperse particles of two types distinguishable by, for example, microscopic examination or photography on the basis of size or by flow cytometry on the basis of size or electrical impedance, e.g. as described in greater detail hereinafter. Alternatively the first form of solid-supported binding partner may, for example, be an appropriately coated dipstick or coated surfaces of the wells of a microtitre plate, with the second form comprising appropriately coated microparticles or beads, these preferably being monodisperse, so that the two forms may be separated and analysed after completion of the assay procedure, e.g. by spectroscopic, radiometric or photographic methods as appropriate. Other alternative systems include use of coated microparticles as the first form and an appropriately coated filter as the second form.

In contrast to the assay procedure described in WO-A-8911101, where the binding partners attached to the two types of particle are required to have the same specificity but different levels of affinity for the analyte, the two forms of solid-supported binding partner used in the method of the present invention may employ the same binding partner. Such use of a single binding partner is preferred, since it simplifies both the procedure and its material requirements, removes the possibility of errors arising from variations in the relative affinities of a pair of binding partners, and permits the procedure to be applied to analytes for which it is difficult to provide pairs of binding partners having the same specificity but different affinity. When applied to particle systems the method of the invention may also exhibit greater flexibility than that of WO-A-8911101 in terms of the ability to optimise parameters such as particle concentrations and incubation times.

It will be appreciated that it may, however, be advantageous in particular applications for the two forms of solid-supported binding partner to differ in specificity and/or affinity, and such procedures are embraced by the invention.

The first form of solid-supported binding partner is preferably used in a relatively low amount in the method of the invention, e.g. in an amount of less than 10% w/w relative to the second form. When it is in the form of coated particles these preferably carry a relatively high loading of the binding partner and are used in relatively low numbers so as to maximise the amount of binding per particle and thereby enhance the sensitivity of the method at low analyte concentrations.

The second form of solid-supported binding partner is preferably used in a relatively high amount, in order to ensure rapid binding of analyte remaining in solution in the sample. Thus the use of a substantial amount of the second form of solid-supported binding partner, e.g. an excess relative to the labelled ligand, is particularly preferred where short overall assay times are desired. The level of loading of binding partner on the solid support is not critical and may be chosen to suit a particular assay system; it may for example be lower than the level for the first form of solid-supported binding partner since the principal contribution of the second form of solid-supported binding partner is at higher analyte concentrations, so that it is not necessary to maximise the level of binding to the second form in the interests of sensitivity, i.e. minimum detectable analyte concentration.

Addition of the second form of solid-supported binding partner in substantial excess will effectively prevent any further binding of analyte to the first form of solid-supported binding partner and so in a sense may be regarded as a type of washing step in which unbound analyte is "washed away" in a quantitatively determinable amount.

The time interval between reaction with the first and second forms of solid-supported binding partner is not critical provided that it is kept substantially constant for a given assay system. Since rapidity of assay is one of the advantages obtainable according to the method of the invention, the interval is preferably kept relatively short, e.g. about 15 minutes to 2 or more hours.

Since addition of the second form of solid-supported binding partner, especially when used in substantial excess, effectively quenches reaction of the analyte with the first form of solid-supported binding partner, the process of the invention avoids any need to allow the first form of solid-supported binding partner to reach equilibrium with the analyte, a process which may take up to e.g. 24 hours in systems where low concentrations of the first form of solid-supported binding partner are used in order to obtain high sensitivity. This a substantial benefit of the method of the invention in that it permits the overall assay to be completed in times which may be as short as e.g. 1 to 2 hours.

For maximum reproducibility, detection of signals in respect of the two forms of labelled ligand-carrying solid-supported binding partner should preferably be conducted at a predetermined time interval after reaction with the second form of solid-supported binding partner, although in many cases this will not be critical in view of the rapid equilibrium preferably achieved by adding a substantial excess of the second form of solid-supported binding partner. Time intervals in the range 5 minutes to 2 hours may therefore be convenient. Automation of the measurement procedure may allow precise analysis after short incubation periods, e.g. by measuring at predetermined intervals under non-equilibrium conditions.

BRIEF DESCRIPTION OF THE DRAWINGS

In the accompanying drawings, which illustrate the invention without in any way limiting the same, FIG. 1 illustrates a representative double standard curve comprising logarithmic plots of analyte concentration against fluorescence intensity for a system in which the two forms of solid-supported binding partner comprise first and second particle types p1 and p2, e.g. having different sizes, the labelled ligand comprises a fluorescent label having affinity for the analyte, and detection is by means of flow cytometry. FIG. 2A represents such a double standard curve obtained experimentally as described in the Example, and FIG. 2B represents the double precision profile for the two curves.

Figure 1:
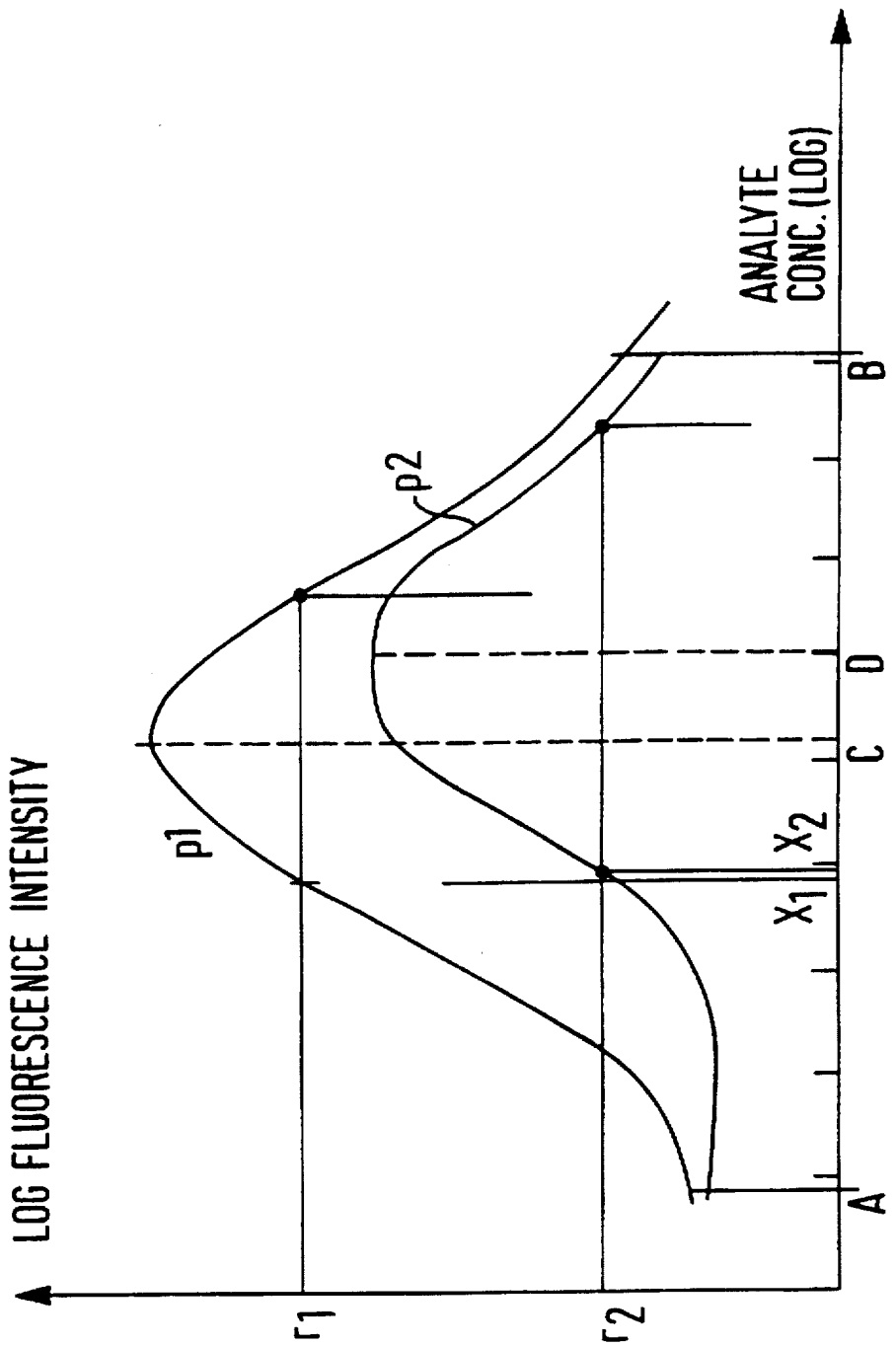
FIG. 1 Logarithmic plots of a double standard curve.

As will be seen from FIG. 1, it is readily possible in such a system to select assay parameters such as the loading of binding partner on particles p1 and p2, the amounts of particles used and the time interval between addition of the two particle types so that the two calibration curves are asymmetrically distributed relative to each other. Similar asymmetrically distributed calibration curves can likewise be obtained in other binary assay systems, e.g. involving microscopic analysis of binary particle systems, use of microtitre plate/microparticle systems, microparticle/filter systems etc.

In the illustrated flow cytometric embodiment the asymmetry of the calibration curves has the effect that for any analyte concentration between points A and B there is a unique and characteristic pair of fluorescence intensity values for the p1 and p2 particles, thus permitting concentration determinations over an exceptionally wide dynamic working range extending well beyond point C corresponding to onset of saturated binding for the p1 particles and point D corresponding to maximum binding of labelled ligand to the p2 particles. An unbiased estimate of an analyte concentration X may be obtained as a linear combination of the two concentrations $x_1$ and $x_2$ determined by the observables $r_1$ and $r_2$ from each of the standard curves, taking into consideration that $r_1$ and $r_2$ should fit the double standard curve as a pair. An improved estimate of the concentration may be determined from the relationship $X=ax_1+(1-a)x_2$, where the value of a is determined by means of statistical theory such that the resulting variance of X is minimal.

It will be apparent from the foregoing that the method of the invention effectively makes practical and positive use of the hook effect to extend its dynamic range, in contrast to prior art procedures such as those of U.S. Pat. No. 4,595,661 and U.S. Pat. No. 4,743,542 which endeavour to postpone or obviate the effect. In this way it may be possible to achieve a working range covering 7–8 decades.

It will be appreciated that embodiments of the method of the invention which employ distinguishable particle types may be used for the simultaneous assay of a plurality of analytes, by using appropriate numbers of labelled ligands, sets of first particle types p1, p1', p1" . . . etc. and sets of second particle types p2, p2', p2" . . . etc., provided that all the individual particle types p1, p1', p1" . . . ., p2, p2', p2" . . . etc. are separately distinguishable, e.g. by flow cytometry, reference being made to an appropriate number of double standard calibration curves for the various p1/p2, p1'/p2', p1"/p2" . . . etc. particle pair combinations.

Such embodiments of the method of the invention may also if desired be adapted to give an indication of levels of non-specific binding in an assay procedure. Thus it is possible to use one or more further distinguishable particle types coated with a binding partner having zero affinity for the analyte(s) to be assayed, e.g. an irrelevant antibody, signals deriving from such particles, e.g. in a flow cytometric analysis, giving a measure of the amount of analyte/label non-specifically bound thereto. It may, for example, be convenient to add a first such further distinguishable particle type (e.g. in a relatively small amount) with the first type particles p1 and any further types p1', p1" . . . etc. and a second such further distinguishable particle type (e.g. in a relatively large amount, if desired in excess or substantial excess relative to the labelled ligand) with the second type particles p2 and any further types p2', p2" . . . etc.

Embodiments of the process of the invention employing distinguishable particle types may additionally or alternatively be adapted to give an indication of the level of unbound labelled ligand remaining after reaction of the sample with one or more sets of p1 and p2 particle types. Typically this may involve addition of one or more further distinguishable particle types p3 having affinity for the labelled ligand(s), e.g. after addition of the p1 and p2 type particles or simultaneously with the p2 type particles, and subsequent detection of signals from these p3 type particles as well as from the p1 and p2 type particles.

It will be appreciated that the quantity of residual unbound labelled ligand so detected will bear a relationship to the analyte concentration, decreasing with increasing analyte concentration in a sandwich assay and increasing with increasing analyte concentration in a competitive assay. Accordingly it is possible to construct a triple standard calibration curve to which p1, p2 and p3 particle signals may be referred in order to give estimates of analyte concentration having even greater precision than is afforded by a double standard curve.

One advantage of this version of the process according to the invention is that the effective "washing away" of unbound labelled ligand by the p3 type particles reduces or may even substantially completely eliminate non-specific binding involving the labelled ligand, thereby minimising or removing a constraint on the sensitivity of the assay system at low analyte concentrations.

In sandwich assays according to this version of the process according to the invention the p3 type particles may conveniently be coated with analyte in order to give the necessary affinity for the labelled ligand. It will be appreciated that the analyte should be bound in such a way that the binding site for which the labelled ligand has affinity remains free to react therewith. It may therefore be convenient initially to coat the p3 type particles with binding partner as is used for the p1 and/or p2 type particles, thereafter permitting analyte to bind to the thus-coated p3 type particles, if desired using a fixative or other crosslinking agent to strengthen the binding. Since the binding partner and labelled ligand normally have affinities for different binding sites on the analyte, analyte bound to the p3 type particles in this way will normally also exhibit affinity for the labelled ligand.

Alternatively the p3 type particles in a sandwich immunoassay system may be coated with an anti-idiotypic antibody which mimics the binding site for which the labelled ligand has affinity.

In competitive assays according to this version of the process according to the invention, where the labelled ligand will have affinity for the binding partner, the p3 type particles may, for example, be coated with a material having affinity for the label part of the labelled ligand, one example here being an anti-FITC antibody.

In general in assays according to the invention which use flow cytometric detection, the various particle types are conveniently distinguished by size, since conventional flow cytometers can determine particle size on the basis of the amount of light scattered by the particles. A wide range of types of monosized particles having different compositions, diameters, reactive surface groups etc. are commercially available, e.g. from Dyno Particles, Lillestrøm, Norway, and appropriate sets of such particles may be used in accordance with the invention. Since such particles are highly monosized, e.g. exhibiting a relative standard deviation not exceeding 1% in light scatter measurements for a sample population, a substantial number of such particle types may be mixed and easily identified as non-overlapping populations in a flow cytometric light scatter histogram.

Use may alternatively or additionally be made of the Coulter principle whereby particles are distinguished by differences in electrical impedance as a result of differences in particle size.

As noted above, it will be necessary when a plurality of analytes is to be assayed simultaneously that all the individual particle types are separately distinguishable, e.g. by flow cytometry. Thus if the same labelled ligand is used for all the analytes it will be necessary for every individual particle type of the various pairs p1/p2, p1'/p2', p1"/p2" . . . etc., any p3 type particles and any particle types carrying irrelevant antibodies to be distinguishable from the other particle types by a detectable particle characteristic. If, on the other hand, different labels are used for each analyte this will permit the various pairs of particle types to be distinguished from each other in terms of qualitative differences in the signals from the labels, e.g. the wavelength of fluorescence signals, so that identically sized particles may if desired be used for all the p1, p1', p1" . . . etc. particle types, a different set of identically sized particles being used for all the p2, p2', p2" . . . etc. particle types. In some cases, e.g. if the analyte is an antibody of a defined specificity, different labels, e.g. with different colours of fluorescence, may be utilised to quantify different amounts of various subclasses of the analyte, e.g. isotype classes of the specific antibody.

Coating of solid support systems for use in the method of the invention can be effected using, for example, procedures standard in the art. Thus, for example, representative techniques for coating monosized particle systems with antibodies for use in immunoassay procedures are described by Frengen et al. in Clin. Chem. 39 (1993), pp. 2174–2181 and the references contained therein, and by Lindmo et al. in J. Immunol. Meth. 126 (1990), pp. 183–189.

Preferred labels for use in the method of the invention include fluorescent substances such as are commonly used in fluorometric flow cytometry, for example fluorescein or phycoerythrin, or fluorochromes for delayed, time-resolved fluorescence. Such labels may if desired be in the form of fluorescently-stained microspheres, e.g. having diameters of 0.10 microns, for example as described by Saunders et al., in Clin. Chem. 31, 2020. Other labels providing a photometric signal include metal-based systems such as sols of colloidal gold particles. Labels capable of providing significant differences in electrical impedance, for example metal (e.g. gold) particles, may also be used to provide signals which may be detected by the Coulter principle, differences in particle type then being determined by size-dependent properties such as light scattering.

As has previously been noted the labelled ligand is normally employed in a predetermined amount and should be such as to have affinity for the binding partner in the case of a competitive binding assay or for the analyte in the case of a sandwich assay. In the latter type of procedure, which represents a preferred feature of the invention, the labelled ligand and binding partner preferably attach to different binding sites (e.g. epitopes) on the analyte.

In general the labelled ligand may be added to the sample before, after or simultaneously with the solid-supported binding partner of either form. One convenient method is to add the sample to a mixture of the labelled ligand and first form of solid-supported binding partner, the second form then being added after a predetermined interval.

The method of the invention may be used to assay a wide range of analytes, the only limiting requirement for a particular analyte being the existence of a specific binding partner therefor which is capable of being coupled to the surfaces of appropriate solid support systems. Analyte and binding partner pairs may, for example, be selected from any of the following combinations, in which either member of the pair may be the analyte and the other the binding partner:

(a) antigen and specific antibody;

(b) hormone and hormone receptor;

(c) hapten and antihapten;

(d) polynucleotide and complementary polynucleotide;

(e) polynucleotide and polynucleotide binding protein;

(f) biotin and avidin or streptavidin;

(g) enzyme and enzyme cofactor; and (h) lectin and specific carbohydrate.

A member from one of the above pairs, e.g. biotin or a hapten, may if desired be attached to some other molecule and the resulting "secondary" analyte may then be assayed in order to determine indirectly the concentration of the "primary" molecule.

Antigens are one category of preferred analytes for use in the method of the invention, the preferred binding partners therefor being monoclonal antibodies.

According to a further feature of the invention there is provided a kit for use in the assay of an analyte in a sample comprising:

(i) two separate forms of solid support systems each carrying or being adapted to carry a binding partner having affinity for the analyte; and (ii) a labelled ligand having affinity for the analyte or binding partner;

the two forms of solid support systems being such that the amounts of labelled ligand becoming bound to each form in an assay procedure may be independently determined.

The two forms of solid support system advantageously comprise sets of monodisperse particles, e.g. having different sizes which may therefore be distinguished by techniques such as flow cytometry. Such particles may be coated with a selected binding partner or may possess absorption sites or reactive groups on their surfaces in order to permit absorption of or coupling to a binding partner of choice. In one preferred version of the kit the two forms of solid support system carry the same binding partner; in other versions the binding partners may be different.

The kits of the invention may if desired contain a plurality of pairs of solid support systems, preferably different types of monodisperse particles, in order to permit the simultaneous assay of a plurality of analytes in a sample.

Kits according to the invention may if desired alternatively or additionally contain one or more further distinguishable solid support systems carrying or adapted to carry a binding partner having zero affinity for the analyte or material having affinity for the labelled ligand (e.g. as hereinbefore described with regard to p3 type particles).

The following non-limitative Example serves to illustrate the invention.

EXAMPLE

The test analyte was α-fetoprotein (AFP), the source being patient serum assayed at the Norwegian Radium Hospital to contain $3 \times 10^6$ kIU/l. A series of standards of known concentration were prepared therefrom by serial dilution with assay buffer (vide infra).

The two forms of solid-supported binding partners comprised macroporous acrylate particles with surface epoxy groups and having diameters of 6.5 and 7.5 μm respectively, developed by SINTEF, Trondheim, Norway and hereinafter respectively referred to as MP 6.5 and MP 7.5. Both particle types were coated with a mouse monoclonal antibody K57 established at the Norwegian Radium Hospital and having affinity for an epitope of AFP, in accordance with the procedure described by Frengen et al. in Clin. Chem. 39 (1993), pp. 2174-2181, using 150 μg K57/mg particles.

The labelled ligand was prepared from a mouse monoclonal antibody K52 established at the Norwegian Radium Hospital and having affinity for a different epitope of AFP. This was reacted with biotin using a molar ratio of biotin to antibody of 10:1, and the resulting biotinylated K52 (at a concentration of 1.9 mg/l) was mixed with streptavidin-R-phycoerythrin (Becton Dickinson) in a ratio of 6:1 v/v.

The assay buffer used in the procedure was phosphate buffered saline containing 10 g bovine serum albumin, 1 g sodium azide and 1 ml Tween 20 per liter.

In each of a series of assay reagent tubes, 40 μl of labelled antibody and 100 μl of assay buffer were mixed with a 20 μl serum sample. After a minimum 15 minutes of incubation, 40 μl of a suspension of MP 6.5 diluted with assay buffer to a concentration of 46 mg/l (~100,000 particles/ml) were added. The mixture was incubated for 1 hour on a horizontal rotational shaker at room temperature whereafter 40 μl of a suspension of MP 7.5 diluted with assay buffer to a concentration of 900 mg/l were added. The tubes were further incubated on the horizontal rotational shaker. Small volumes of the contents of each tube were measured by a flow cytometer after 1 and 2 hours incubation, without prior washing.

Flow cytometric fluorescence and light scatter measurements were performed using a Skatron Argus Flow Cytometer equipped with a 75 watt mercury-xenon lamp. The filterblock used provided excitation in the wavelength range 510-560 nm and fluorescence measurements in the range 590-640 nm. Particle-associated light scatter and fluorescence signals were measured simultaneously and registered as correlated two-parameter histograms. By gating on appropriate windows in the light scatter histogram, fluorescence intensity histograms of the different particle types were obtained. The median channel of the logarithmic fluorescence histogram was taken as a measure for the particle-associated fluorescence.

Figure 2A:
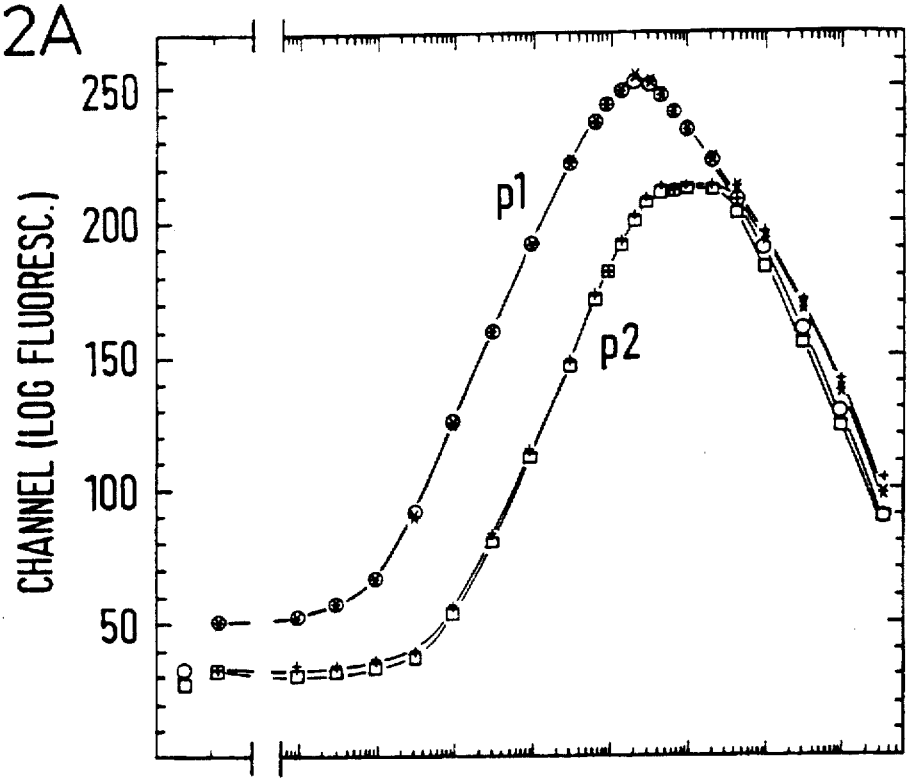
FIGS. 2A–B A double standard curve and precision profile for results from the Example.

The simultaneously-measured standard curves for MP 6.5 (p1) particles and MP 7.5 (p2) particles after 1 and 2 hours final incubation are shown in FIG. 2A, results for MP 6.5 after 1 hour final incubation being represented by circles, results for MP 6.5 after 2 hours final incubation being represented by asterisks, results for MP 7.5 after 1 hour final incubation being represented by squares and results for MP 7.5 after 2 hours final incubation being represented by crosses. Other data (not shown) representing different incubation times after addition of the MP 7.5 (p2) particles confirm the effective arresting effect that this addition has on further binding of analyte to p1, and also show that equilibrium is quickly achieved after addition of p2.

The results in FIG. 2A show that binding to both the MP 6.5 and MP 7.5 particles is practically constant over these time intervals for AFP concentrations below 30,000 kIU/l. At higher analyte concentrations, prolonged incubation yields moderately increased binding to both particle types.

Figure 2B:
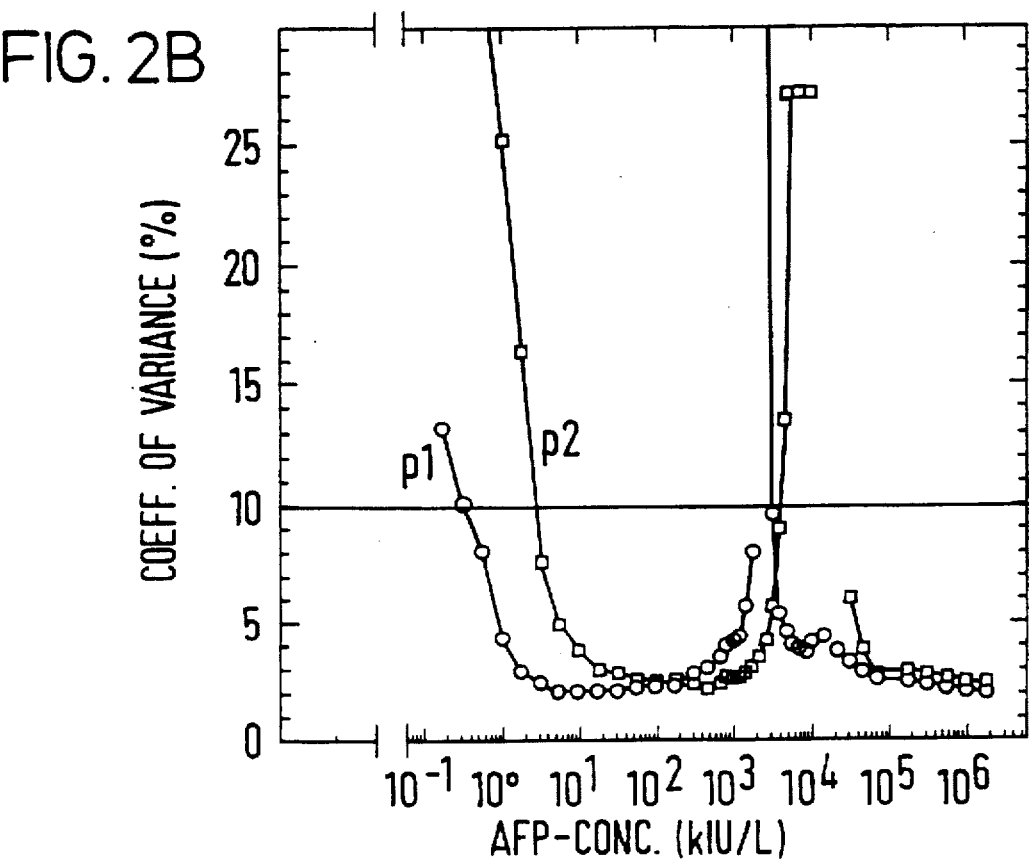

The precision profiles for the MP 6.5 and MP 7.5 particles as shown in FIG. 2B are expressed in terms of the coefficient of variance (CV):

$$CV = \sigma_{R_i} * [\delta(\ln D)/\delta R_i] * 100[\%]$$

where $R_i$ is the measured response of particle (i) expressed as channel number of logarithmic fluorescence intensity, $\sigma_{R_i}$ is the corresponding standard deviation obtained from two parallel assays for each standard, using a 1 hour final incubation, and D denotes the dose (i.e. concentration of AFP).

The precision profiles for the MP 6.5 and MP 7.5 particles show that either one or both standard curves provide a CV<10% throughout the concentration range $<0.6 \to 3 \times 10^6$ kIU/l AFP.

The low concentration of MP 6.5 used assures high sensitivity. The use of MP 7.5 particles at 20 times higher concentration yields poorer sensitivity, but the response in respect of this particle increases beyond the AFP concentration at which the MP 6.5 standard curve begins to decline. Thus the two standard curves taken together provide unambiguous determination of AFP concentrations over the range <0.6–>3×10$^6$ kIU/l.

I claim:

1. In a method for assaying an analyte in a sample comprising reacting the sample with two independently determinable forms of solid-supported binding partner having affinity for the analyte and with a labelled ligand having affinity for the analyte or the binding partner, thereby yielding two forms of labelled ligand-carrying solid-supported binding partner, said two independently determinable forms of solid-supported binding partner being such that signals in respect of said two forms of labelled ligand-carrying solid-supported binding partner may be independently determined whereby the analyte concentration may be obtained by reference to a double standard calibration curve, wherein the improvement comprises adding to the sample the first form of solid-supported binding partner and then after an interval adding the second form of solid-supported binding partner.

2. A method as claimed in claim 1 wherein the solid supports for said two forms of solid-supported binding partner comprise two distinguishable types of monodisperse particles.

3. A method as claimed in claim 2 wherein said two types of monodisperse particles are distinguishable by size.

4. A method as claimed in claim 2 wherein said two types of monodisperse particles are detected by flow cytometry.

5. A method as claimed in claim 1 wherein the first form of solid-supported binding partner is used in a low amount relative to the second form of solid-supported binding partner.

6. A method as claimed in claim 1 wherein the second form of solid-supported binding partner is used in excess relative to the labelled ligand.

7. A method as claimed in claim 2 wherein one or more further distinguishable types of monodisperse particles coated with a binding partner having zero affinity for the analyte are also added and signals deriving therefrom are used to give a measure of non-specific binding of analyte, labelled ligand or a combination thereof to said zero affinity partner.

8. A method as claimed in claim 2 wherein one or more further distinguishable types of monodisperse particles coated with material having affinity for the labelled ligand are also added and signals deriving therefrom are used to give a measure of residual unbound labelled ligand or unbound labelled ligand-analyte complex.

9. A method as claimed in claim 2 wherein a plurality of analytes is simultaneously assayed using an appropriate number of labelled ligands and sets of distinguishable particle types.

10. A method as claimed in claim 1 wherein the label component of the labelled ligand is a fluorescent substance.

11. A method as claimed in claim 1 wherein the analyte is an antigen and the binding partner therefor is a monoclonal antibody.

12. A method as claimed in claim 1 wherein the same binding partner is employed in the two independently determinable forms of solid-supported binding partner.

* * * * *